(12) United States Patent
Kiesele

(10) Patent No.: US 6,695,959 B2
(45) Date of Patent: Feb. 24, 2004

(54) ELECTROCHEMICAL GAS SENSOR WITH NONPLANAR DIFFUSION MEMBRANE AND ELECTRODE ARRAY

(75) Inventor: Herbert Kiesele, Lübeck (DE)

(73) Assignee: Drägerwerk Aktiengesellschaft, Lübeck (DE)

( * ) Notice: Subject to any disclaimer, the term of this patent is extended or adjusted under 35 U.S.C. 154(b) by 0 days.

(21) Appl. No.: 10/316,617

(22) Filed: Dec. 11, 2002

(65) Prior Publication Data
US 2003/0159930 A1 Aug. 28, 2003

(30) Foreign Application Priority Data
Feb. 25, 2002 (DE) .......................... 102 08 074

(51) Int. Cl.[7] ............................................ G01N 27/404
(52) U.S. Cl. .................... 204/415; 204/412; 204/431
(58) Field of Search ................. 204/412, 415, 204/431; 205/782, 782.5, 783

(56) References Cited

U.S. PATENT DOCUMENTS

| 3,239,444 A | * | 3/1966 | Heldenbrand |
| 3,719,575 A | * | 3/1973 | Niedrach et al. |
| 3,755,125 A | * | 8/1973 | Shaw et al. |
| 3,954,590 A | * | 5/1976 | Czuha |
| 4,259,165 A | * | 3/1981 | Miyake |
| 4,790,925 A | * | 12/1988 | Miller et al. |
| 4,909,908 A | * | 3/1990 | Ross et al. |
| 5,298,146 A | | 3/1994 | Braden et al. |
| 5,395,507 A | * | 3/1995 | Aston et al. |
| 5,401,376 A | * | 3/1995 | Foos et al. |
| 5,723,036 A | * | 3/1998 | Chrzan et al. |

FOREIGN PATENT DOCUMENTS

| DE | 41 36 779 | 5/1993 |
| DE | 41 31 826 | 7/1993 |
| DE | 195 33 911 | 5/1996 |
| DE | 43 35 409 | 9/1996 |
| DE | 44 38 524 | 9/1996 |

* cited by examiner

Primary Examiner—T. Tung
(74) Attorney, Agent, or Firm—McGlew and Tuttle, P.C.

(57) ABSTRACT

An electrochemical gas sensor, which has a substantially more compact design and is manufactured with a considerably reduced manufacturing effort. A conical, calotte-shaped, hemispherical or cylindrical outer housing is provided with gas admission openings (3, 203). A cover (8, 208) as well as a layer structure is provided with, from the outside to the inside, the diffusion membrane (4, 204) with the electrodes (5, 6, 7; 205, 206, 207) applied thereto in a planiform manner, a layer (11, 211) consisting of a mat material or a porous body, which accommodates the electrolyte, and an electrolyte space (10, 210), which is filled at least partially with the electrolyte.

20 Claims, 6 Drawing Sheets

ELECTROCHEMICAL GAS SENSOR WITH NONPLANAR DIFFUSION MEMBRANE AND ELECTRODE ARRAY

FIELD OF THE INVENTION

The present invention pertains to an electrochemical gas sensor with at least two electrodes, a diffusion membrane and an electrolyte, and relates to a process for making same.

BACKGROUND OF THE INVENTION

Such a gas sensor is shown in DE 43 35 409 C2, where the housing jacket surrounding the electrolyte space is designed as a barrier, which is permeable to gases with respect to the environment but is impermeable to the electrolyte and via which pressure equalization takes place between the electrolyte space and the environment without the electrolyte being able to run out. In this gas sensor and in other prior-art gas sensors, the electrodes used are introduced into the sensor housing separately and individually and are contacted by means of suitable wires or pins, and the electric contacts are led to the outside through the sensor housing. The electrodes are arranged stacked at spaced locations from one another. Special separators in the form of, e.g., porous, electrolyte-impregnated glass mats are used for this purpose, so that no electric short-circuit can develop between the electrodes. These prior-art electrochemical gas sensors require a great, predominantly manual effort for their assembly, which is, moreover, complicated and may lead to errors.

The prior-art gas sensor of this type with a gas-permeable housing offers the following advantages in practice: It guarantees a position-independent pressure equalization between the interior space of the sensor and the environment, high chemical resistance as well as very good tightness properties, as a consequence of which the measurement of the concentration of the measured gas or measured gases is highly reliable, and the service life is long.

SUMMARY OF THE INVENTION

It is an object of the present invention to provide a gas sensor with the known properties, which has a more compact design in terms of size and can be manufactured with a reduced manufacturing effort and consequently at a lower cost.

According to the invention, an electrochemical gas sensor is provided with at least two electrodes, a diffusion membrane and an electrolyte. The gas sensor has a conical, hemispherical or cylindrical outer housing with gas admission openings and with a cover. A layer structure is provided comprising, from the outside to the inside, the diffusion membrane with the electrodes applied thereto in a planiform manner, a layer of a mat material or a porous body, which accommodates the electrolyte, and an electrolyte space filled at least partially with the electrolyte.

An advantage of the present invention is the use of a nonplanar diffusion membrane and of a nonplanar electrode array in the gas sensor. All electrodes, i.e., the measuring electrode, the reference electrode and optionally the auxiliary electrode, are first applied alternatively, optionally with the associated strip conductors or contact paths, either to a cone envelope-shaped or circular, planar diffusion membrane or to a rectangular, likewise planar diffusion membrane. The cone envelope-shaped or circular diffusion membrane is subsequently welded into a rounded cone envelope-shaped or calotte-shaped or hemisphere-shaped housing part, and the rectangular diffusion membrane is alternatively welded into a cylindrical housing part. The electrodes are covered with a mat that is absorbent with respect to the electrolyte or with a porous body. Electrolyte is subsequently filled into the rounded cone envelope-shaped or calotte-shaped or hemisphere-shaped or alternatively cylindrical array, and the housing is closed with a flat cover. The contacting with a plug for the connection to an external evaluating unit is performed from the outside via the strip conductors or the contact paths. The leakage of electrolyte through this opening for the electric contacting can be reliably prevented from occurring by means of a suitable, prior-art sealing material. Another essential advantage of the present invention arises from the fact that the diffusion membrane accommodating the electrodes and their electric lines can be manufactured in an automated manner at low cost, so that the complicated and time-consuming assembly of the individual components, which has hitherto been usual, is considerably simplified.

More than one measuring electrode may be provided for the simultaneous measurement of more than one measured gas with a said measured gas-specific measuring electrode for each.

The gas admission openings may advantageously be located in the area of the maximum distance from the cover. The housing with the cover may consist of a gas-impermeable material, especially polypropylene, polyethylene, polystyrene, polycarbonate, PMMA (polymethyl methacrylate), PSU (polysulfone), FEP (copolymer from hexafluoropropylene and tetrafluoropropylene), or PFA (perfluoroalkoxy polymer). The housing may be designed in the form of a hemisphere or a cylinder with semicircular or U-shaped cross-sectional area.

The mat material may be a polymer material, glass, quartz or ceramic fibers, and the porous body may be formed of the same materials.

Electric lines associated with the electrodes may be applied to the diffusion membrane in the form of contact paths or strip conductors. The electrodes and/or the electric lines may be printed, sintered, sputtered or vapor-deposited on the said diffusion membrane.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
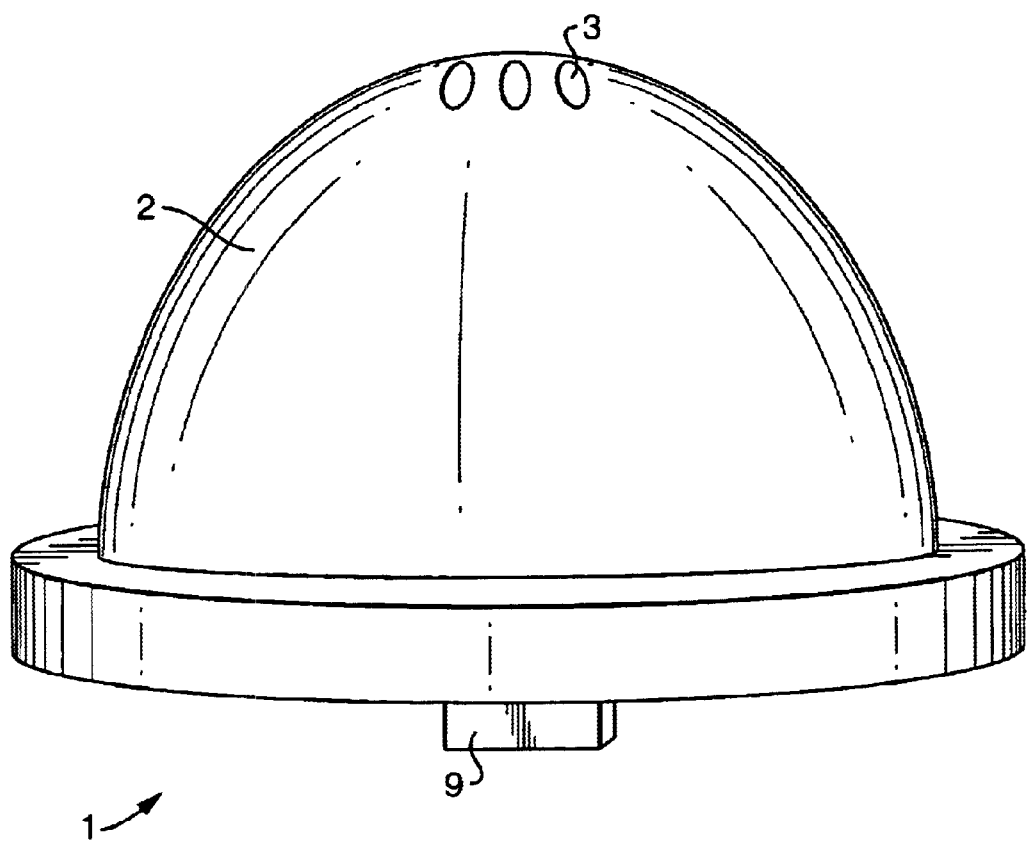
FIG. 1 is a view of a first electrochemical gas sensor with a housing of hemispherical design and with a nonplanar diffusion membrane and electrode array.
Figure 2:
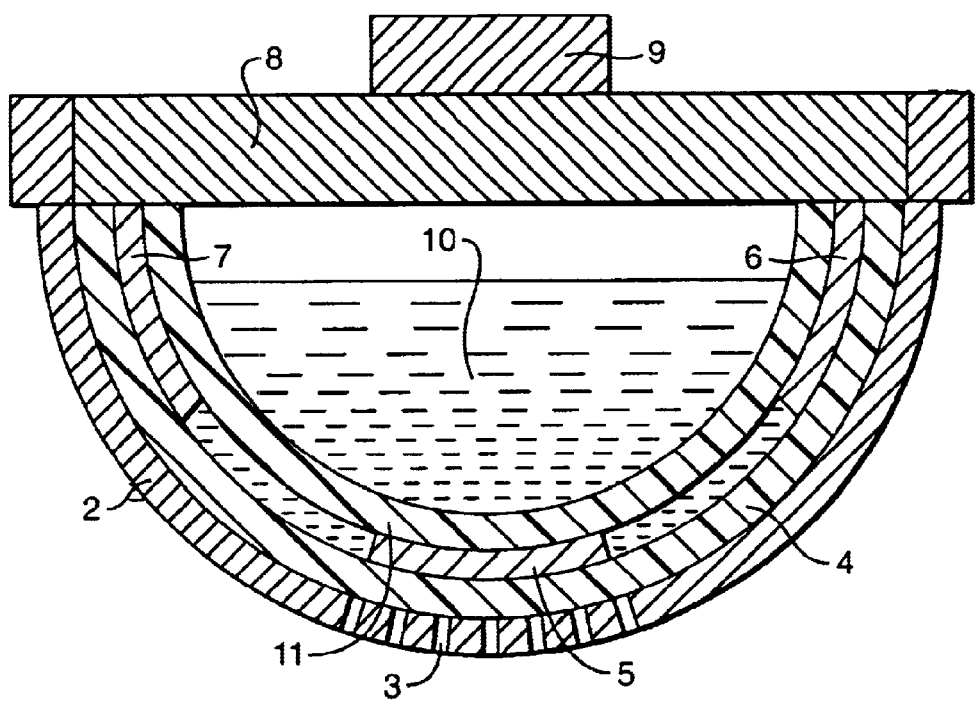
FIG. 2 is a vertical sectional view through the gas sensor according to FIG. 1.
Figure 3:
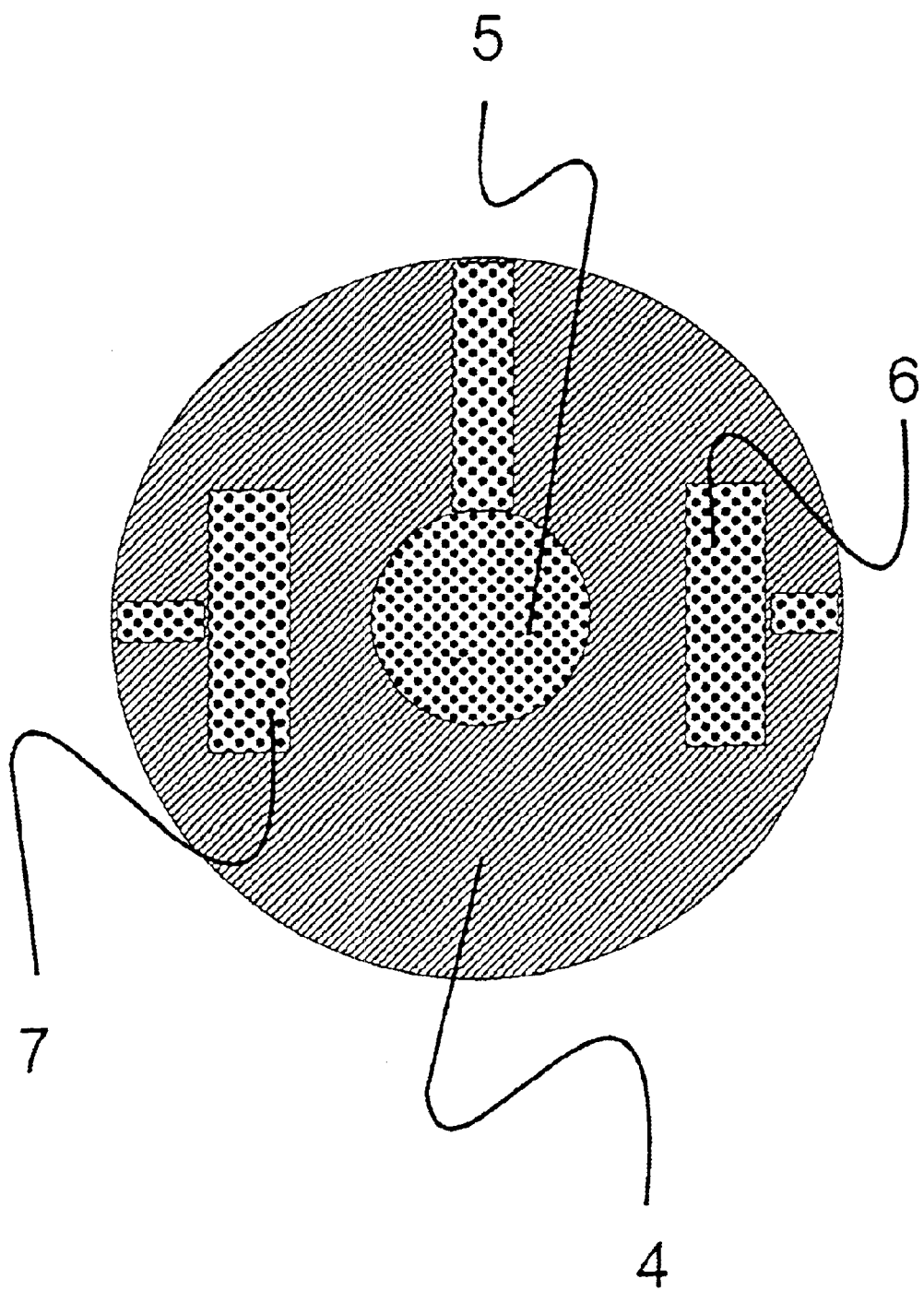
FIG. 3 is a top view of a circular diffusion membrane with applied electrodes and strip conductors before the introduction into the gas sensor according to FIG. 1.

Referring to the drawings in particular, the electrochemical gas sensor 1 according to FIG. 1 has an outer housing 2, which is of a hemispherical design, but may alternatively also be calotte-shaped or have a shape similar to the above-mentioned geometric shapes. The housing 2 consists of a gas-impermeable material, especially polypropylene, polyethylene, polystyrene, polycarbonate, PMMA (polymethyl methacrylate), PSU (polysulfone), FEP (copolymer from hexafluoropropylene and tetrafluoropropylene) or PFA (perfluoroalkoxy polymer). The housing 2 has a plurality of gas admission openings 3 for the entry of the gas to be measured, whose concentration is to be determined by means of the electrochemical gas sensor 1. The housing 2 is closed with a flat cover 8 (FIG. 2) and has a plug 9 for connection to an external evaluating unit. The design of the gas sensor 1 is shown in FIG. 2: The cover 8 is connected to the housing 2 such that the electric lines between the cover 8 and the housing 2, which are associated with the electrodes 5, 6, 7, are led from the gas sensor 1 to the plug 9, and the electrolyte can be prevented from leaking by embedding in sealing material. The design is such from the outside to the inside that the diffusion membrane 4, which consists of a hydrophobic material, which is permeable to the gas to be measured but is impermeable to the electrolyte (e.g., PTFE), is welded into the housing 2. The electrodes 5, 6, 7 with associated strip conductors or contact paths are optionally printed on the diffusion membrane 4 in a preceding step as is shown in FIG. 3. The measuring electrode 5, the reference electrode 6 and the auxiliary electrode 7 are applied to the diffusion membrane 4 such that they are in contact with the layer 11 consisting of a mat material or a porous body for accommodating an electrolyte. The strip conductors or contact paths are preferably provided with an insulating layer, so that a disturbance in the measured signals generated between the electrodes 5, 6, 7 after the diffusion of the measured gas through the diffusion membrane 4 is prevented from occurring. The mat material consists of a polymer material, glass, quartz or ceramic fibers, and the porous body is made of the same materials. The electrolyte space 10 is filled at least partially with the electrolyte, which is also located in the layer 11. The housing 2 is closed with the cover 8 such that the gas sensor 1 can be used in a liquid medium or in a gaseous environment for measuring the concentration of the gas to be measured, i.e., the measured gas. The measured gas, which may also consist of a plurality of components, diffuses through the diffusion membrane 4 in the area of the gas admission openings 3 in a controlled manner, and the measurement at the electrodes 5, 6, 7 printed, sintered, sputtered or vapor-deposited on the diffusion membrane 4 leads to the determination of the concentration of the measured gas via electrochemical reactions, which are known per se, and whose signals are evaluated separately outside the housing 2.

Figure 4:
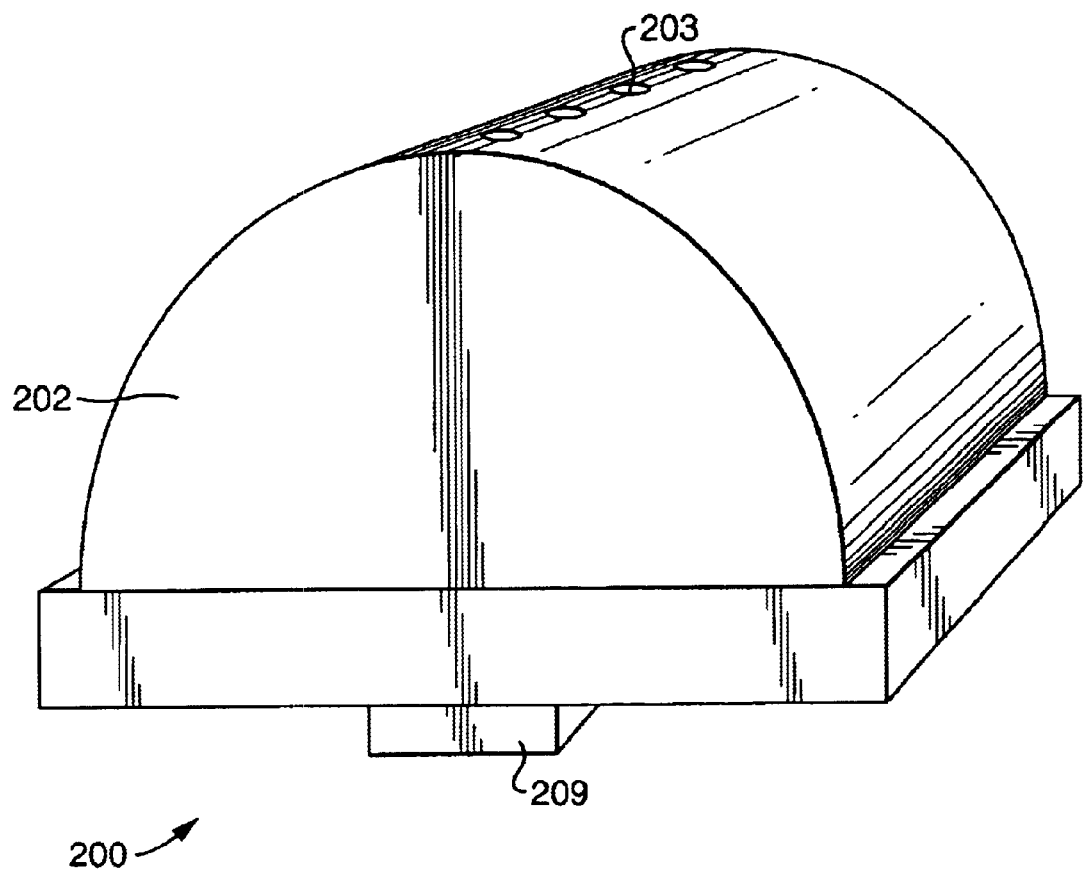
FIG. 4 is a view of a second electrochemical gas sensor with a housing of cylindrical design and with a nonplanar diffusion membrane and electrode array.

The second electrochemical gas sensor 200 according to FIG. 4 is provided with a cylindrical housing 202, which is provided with semicircular end faces, which are parallel to one another in the exemplary embodiment. The cross-sectional area may also be U-shaped or in the form of an only partially approximated semicircle or a semicircle section. The plug 209 is located at the flat cover 208 (FIG. 5).

Figure 5:
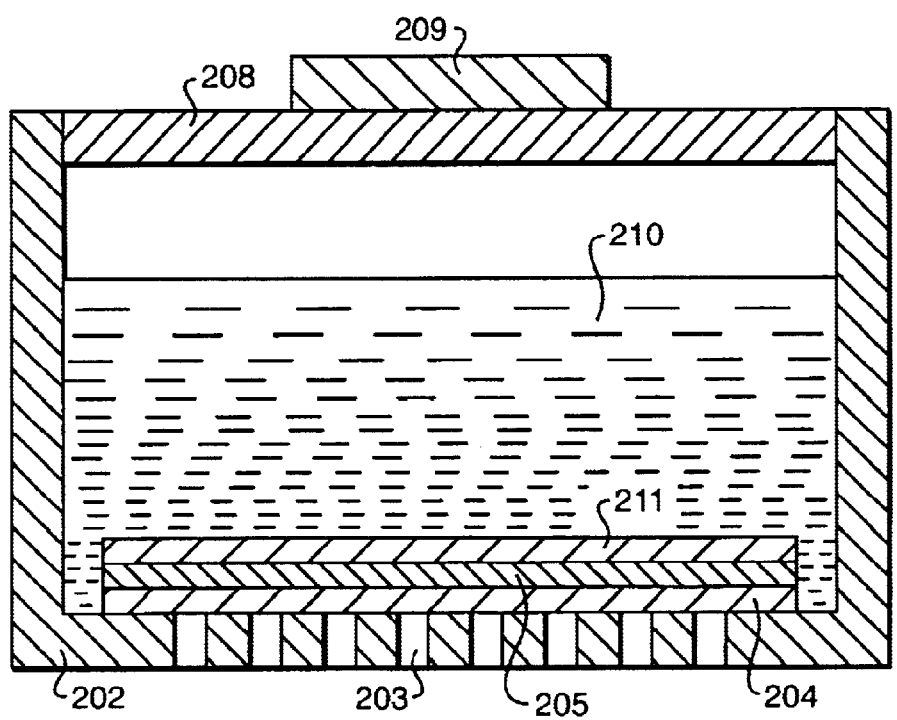
FIG. 5 is a vertical section through the central longitudinal axis of the gas sensor according to FIG. 4.
Figure 6:
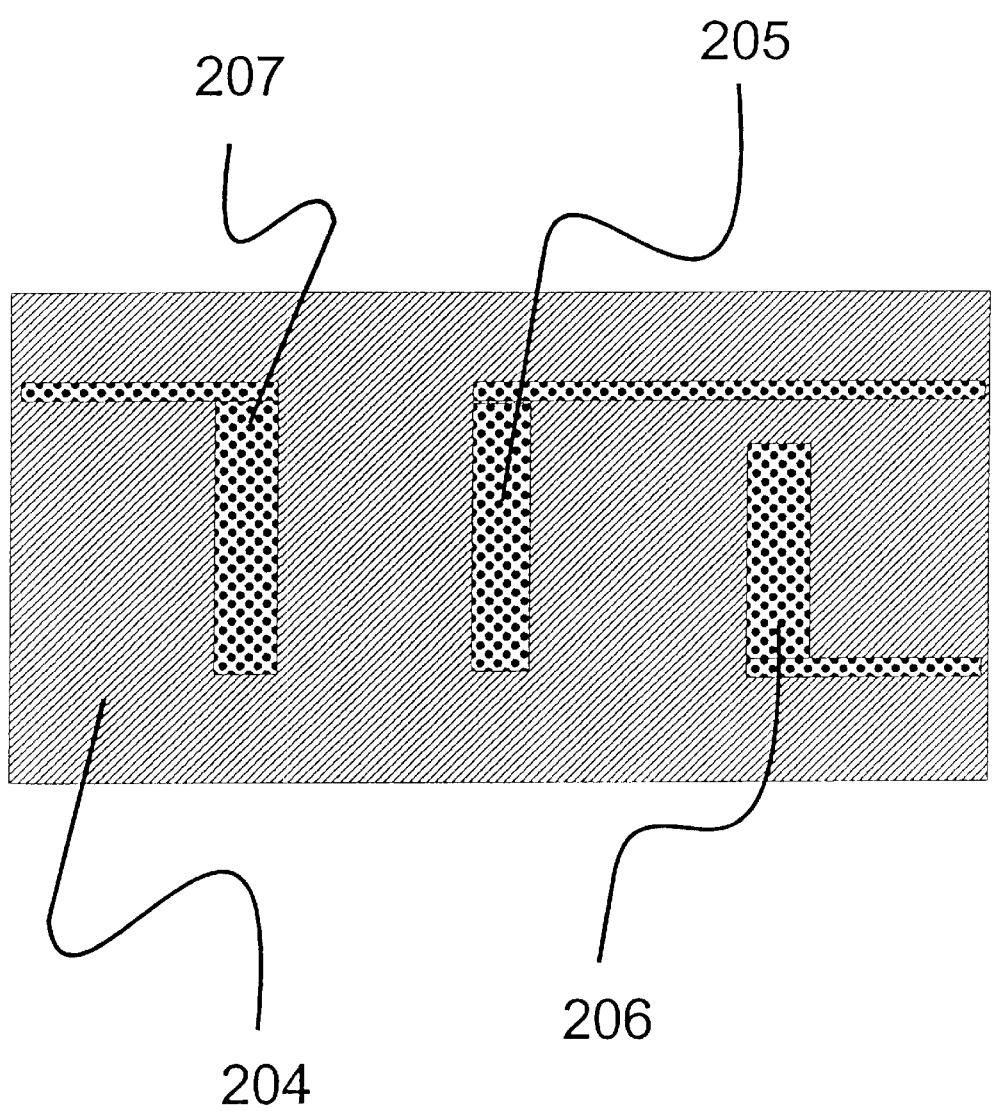
FIG. 6 is a top view of a rectangular diffusion membrane with applied electrodes and strip conductors before the introduction into the gas sensor according to FIG. 4.

While FIG. 5 shows a vertical sectional view along the central longitudinal axis of the gas sensor 200 from FIG. 4, the layer structure is analogous in a sectional view at right angles to the longitudinal axis to that shown in FIG. 2 and is therefore not shown separately. The diffusion membrane 204 is followed, from the outside to the inside, by the measuring electrode 205, the layer 211, which consists of a mat material or a porous substrate and is impregnated with electrolyte, as well as the electrolyte space 210 with the same electrolyte. FIG. 6 shows the rectangular diffusion membrane 204, which is still planar according to this embodiment, with the electrodes 205, 206, 207, namely, the measuring electrode 205, the reference electrode 206 and the auxiliary electrode 207 and with associated strip conductors or contact paths, which were applied in a step preceding the assembly of the sensor proper. The diffusion membrane 204 is subsequently welded or bonded into the housing 202. The electrodes 205, 206, 207 are covered with the layer 211, which is loaded with electrolyte after the electrolyte space 210 has been finally filled with electrolyte. Finally, the gas sensor 200 is closed with the flat cover 208.

While specific embodiments of the invention have been shown and described in detail to illustrate the application of the principles of the invention, it will be understood that the invention may be embodied otherwise without departing from such principles.

What is claimed is:

1. An electrochemical gas sensor, comprising:

two electrodes;

a diffusion membrane;

an electrolyte, an outer housing with a conical, hemispherical or cylindrical outer housing shape and with gas admission openings;

a cover connected with said outer housing: and a layer structure comprising, from adjacent to said outer housing with gas admission openings in a direction away from said outer housing with gas admission openings to-the-inside, the diffusion membrane with the two electrodes applied thereto in a planiform manner and a layer of a mat material or a porous body, which accommodates the electrolyte, an electrolyte space filled at least partially with the electrolyte, the electrolyte space being defined by said layer structure adjacent to said layer of mat material or porous body.

2. An electrochemical gas sensor in accordance with claim 1, wherein said two electrodes include a measuring electrode and the electrochemical gas sensor further comprising another measuring electrode, said measuring electrode and said another measuring electrode being each a gas-specific measuring electrode for the simultaneous measurement of more than one measured gas.

3. An electrochemical gas sensor in accordance with claim 1, wherein the gas admission openings are located in an area of maximum distance from the cover.

4. An electrochemical gas sensor in accordance with claim 1, wherein the housing and said cover consist of a gas-impermeable material formed of one of polypropylene, polyethylene, polystyrene, polycarbonate, PMMA (polymethyl methacrylate), PSU (polysulfone), FEP (copolymer from hexafluoropropylene and tetrafluoropropylene) and PFA (perfluoroalkoxy polymer).

5. An electro chemical gas sensor in accordance with claim 1, wherein the housing is designed in the form of a hemisphere or a cylinder with a semicircular or U-shaped cross-sectional area.

6. An electrochemical gas sensor in accordance with claim 1, wherein the mat material or the porous body consists of one or more of a polymer material, glass, quartz fibers and ceramic fibers.

7. An electrochemical gas sensor in accordance with claim 1, wherein electric lines associated with the electrodes are applied to the diffusion membrane in the form of contact paths or strip conductors.

8. An electrochemical gas sensor in accordance with claim 7, wherein the electrodes and/or the electric lines are printed, sintered, sputtered or vapor-deposited on the diffusion membrane.

9. A method of forming an electrochemical gas sensor, comprising:

providing first and second electrodes, a diffusion membrane and an electrolyte, forming an outer housing with a conical, hemispherical or cylindrical outer housing shape and with gas admission openings;

providing a cover; and forming a layer structure within the outer housing with the layer structure comprising, from the outside to the inside, the diffusion membrane with the two electrodes applied thereto in a planiform manner and a layer of a mat material or a porous body, which accommodates the electrolyte, the layer structure adjacent to said mat material or a porous body forming an electrolyte space filled at least partially with the electrolyte.

10. An electrochemical gas sensor, comprising:

an outer housing with gas admission openings;

a cover connected with said outer housing;

an electrolyte; and a layer structure comprising a diffusion membrane adjacent to said outer housing, two electrodes applied in a substantially planiform manner to said diffusion membrane on a side opposite said admission openings and a layer adjacent to said electrodes, said layer being of a mat material or a porous body which accommodates the electrolyte, said cover being connected to said outer housing to delimit an exterior of the electrochemical gas sensor with a conical, hemispherical or cylindrical exterior shape with said layer structure conforming to the shape of the outer housing and cooperating with said cover to define an electrolyte space adjacent to said layer of a mat material or a porous body, the electrolyte space being at least partially filled with a portion of said electrolyte.

11. An electrochemical gas sensor in accordance with claim 10, wherein said two electrodes include a measuring electrode and the electrochemical gas sensor further comprising another measuring electrode, said measuring electrode and said another measuring electrode being each a gas-specific measuring electrode for the simultaneous measurement of more than one measured gas with one measured gas-specific measuring electrode each.

12. An electrochemical gas sensor in accordance with claim 10, wherein the gas admission openings are located in an area of maximum distance from the cover.

13. An electrochemical gas sensor in accordance with claim 10, wherein the housing and said cover consist of a gas-impermeable material formed of one of polypropylene, polyethylene, polystyrene, polycarbonate, PMMA (polymethyl methacrylate), PSU (polysulfone), FEP (copolymer from hexafluoropropylene and tetrafluoropropylene) and PFA (perfluoroalkoxy polymer).

14. An electrochemical gas sensor in accordance with claim 10, wherein the housing is designed in the form of a hemisphere or a cylinder with a semicircular or U-shaped cross-sectional area.

15. An electrochemical gas sensor in accordance with claim 10, wherein the mat material or the porous body consists of one or more of a polymer material, glass, quartz fibers;

(and ceramic fibers.

16. An electrochemical gas sensor in accordance with claim 10, wherein electric lines associated with the electrodes are applied to the diffusion membrane in the form of contact paths or strip conductors.

17. An electrochemical gas sensor in accordance with claim 16, wherein the electrodes and/or the electric lines are printed, sintered, sputtered or vapor-deposited on the diffusion membrane.

18. A method of forming an electrochemical gas sensor, comprising:

providing an outer housing with gas admission openings;

providing a cover;

forming a layer structure on an inner surface of the outer housing with a diffusion membrane adjacent to said outer housing, two electrodes applied to said diffusion membrane in a planiform manner on a side of said diffusion membrane opposite said outer housing and a layer of a mat material or a porous body;

providing a cover;

providing electrolyte; and disposing the outer housing with the layer structure in one of a conical, hemispherical or cylindrical outer housing shape with the layer structure defining an electrolyte space and with the layer structure conforming to the shape of the outer housing;

filling the electrolyte space with the electrolyte;

and closing the electrolyte space with the cover by connecting the cover to the outer housing.

19. A method in accordance with claim 18, wherein electric lines associated with the electrodes are applied to the diffusion membrane in the form of contact paths or strip conductors.

20. A method in accordance with claim 19, wherein the electrodes and/or the electric lines are printed, sintered, sputtered or vapor-deposited on the diffusion membrane.

* * * * *